(12) United States Patent
Ella et al.

(10) Patent No.: US 8,642,107 B2
(45) Date of Patent: Feb. 4, 2014

(54) WATER FORMULATION WITH HERBAL HINT AND A PROCESS THEREFOR

(75) Inventors: Murthy Krishna Ella, Malur (IN); Suchitra Ella, Malur (IN); Alwar Ananda Purushotham Rudrapattana, Malur (IN); Gopal Vinaya Kaippangala, Malur (IN); Smita Singhania, Malur (IN)

(73) Assignee: Century Biologicals Private Limited, Malur (IN)

( * ) Notice: Subject to any disclaimer, the term of this patent is extended or adjusted under 35 U.S.C. 154(b) by 462 days.

(21) Appl. No.: 12/438,344

(22) PCT Filed: Jul. 11, 2007

(86) PCT No.: PCT/IN2007/000287
§ 371 (c)(1),
(2), (4) Date: Feb. 20, 2009

(87) PCT Pub. No.: WO2008/023387
PCT Pub. Date: Feb. 28, 2008

(65) Prior Publication Data
US 2010/0009038 A1    Jan. 14, 2010

(30) Foreign Application Priority Data

Aug. 23, 2006 (IN) .......................... 1495/CHE/2006

(51) Int. Cl.
*A23L 2/00* (2006.01)

(52) U.S. Cl.
USPC ......................................................... 426/590

(58) Field of Classification Search
USPC ......................................................... 426/590
See application file for complete search history.

(56) References Cited

U.S. PATENT DOCUMENTS

| 4,835,002 A * | 5/1989 | Wolf et al. ................. 426/590 |
| 4,880,639 A * | 11/1989 | Lauermann et al. .......... 426/2 |
| 2003/0228384 A1 | 12/2003 | Kurk et al. ................... 424/745 |
| 2006/0029705 A1 * | 2/2006 | McPherson et al. ......... 426/534 |

FOREIGN PATENT DOCUMENTS

| DE | 202007007584 U1 * | 9/2007 |
| EP | 1 696 747 * | 6/2006 |
| KR | 2001 0007764 A | 2/2001 |
| WO | PCT/IB03/06189 * | 4/2005 |
| WO | 2005/070236 A | 8/2005 |
| WO | 2006/068065 A | 6/2006 |

* cited by examiner

*Primary Examiner* — Patricia George
(74) *Attorney, Agent, or Firm* — Emerson Thomson Bennett, LLC; Roger D. Emerson; Sergey Vernyuk (57) ABSTRACT

A method and formulation for drinking water with herbal hint, in particular for packaged drinking water with herbal hint, is provided. The formulation includes water, wherein the water satisfies the pre-specified standards of drinking water. Further, the formulation includes one or more herbal ingredients. Also, the formulation includes essential oil of Rosemary to stabilize the formulation and hence to increase its shelf life.

1 Claim, 6 Drawing Sheets

REAL TIME SHELF LIFE STUDIES - EXTENDED FLAVOUR INTENSITY OF DIFFERENT ESSENTIAL OILS

Note:
Treatment No. 1 – Rosemary + Vetiver.
Treatment No. 2 – Rosemary + Patchouli.
Treatment No. 3 – Rosemary + Geranium.
Treatment No. 4 – Rosemary + Palmarosa.
Treatment No. 5 – Rosemary + Menthol Mint.

Fig. 1

REAL TIME SHELF LIFE STUDIES - EXTENDED FLAVOUR INTENSITY OF DIFFERENT ESSENTIAL OILS

Note:

Treatment No. 1 – Rosemary + Vetiver.
Treatment No. 2 – Rosemary + Patchouli.
Treatment No. 3 – Rosemary + Geranium.
Treatment No. 4 – Rosemary + Palmarosa.
Treatment No. 5 – Rosemary + Menthol Mint.

Note:

Treatment No. 1 – Rosemary + Palmarosa
Treatment No. 2 – Palmarosa alone [At a known concentration]
Treatment No. 3 – Palmarosa alone [Increased level of known concentration]
Treatment No. 4 – Palmarosa alone [Increased level of known concentration]
Treatment No. 5 – Palmarosa alone [Increased level of known concentration]

REAL TIME SHELF LIFE STUDIES - EXTENDED FLAVOUR INTENSITY OF PATCHOULI ESSENTIAL OIL IN COMBINATION AND ALONE

Note:

Treatment No. 1 – Rosemary + Patchouli
Treatment No. 2 – Patchouli alone [At a known concentration]
Treatment No. 3 – Patchouli alone [Increased level of known concentration]
Treatment No. 4 – Patchouli alone [Increased level of known concentration]
Treatment No. 5 – Patchouli alone [Increased level of known concentration]

Fig. 5

REAL TIME SHELF LIFE STUDIES - EXTENDED FLAVOUR INTENSITY OF MENTHOL MINT ESSENTIAL OIL IN COMBINATION AND ALONE

Note:

Treatment No. 1 – Rosemary + Menthol Mint.
Treatment No. 2 – Menthol Mint alone [At a known concentration]
Treatment No. 3 – Menthol Mint alone [Increased level of known concentration]
Treatment No. 4 – Menthol Mint alone [Increased level of known concentration]
Treatment No. 5 – Menthol Mint alone [Increased level of known concentration]

Fig. 6

WATER FORMULATION WITH HERBAL HINT AND A PROCESS THEREFOR

FIELD OF THE INVENTION

The present invention relates to the field of drinking water, more particularly, to the field of packaged drinking water, and more particularly, to preparation and formulation of packaged drinking water with an herbal hint. Further, the water of the present invention is also capable of providing health benefits.

BACKGROUND OF THE INVENTION

Clean water is essential to human health and in many parts of the world it is in limited supply. Water that is fit for human consumption is called drinking water or potable water. Water that is not specifically made for drinking, but is not harmful for human, when used for food preparation is called safe water.

Water as a natural resource is becoming scarcer in certain places, and its availability is a major social and economic concern. However, the tendency of people to use safe drinking water is on the increase due to the knowledge and importance of drinking safe water to preserve their health and to avoid water borne diseases. In order to get safe water, people opt for packaged drinking water. The packaged drinking water shall conform to certain standards namely with respect to physical, chemical and microbiological parameters. The packaged drinking water is normally derived from any source of potable water which is subjected to one or more treatments, namely, decantation, filtration, combination of filtration, aerations, filtration with membrane filter, depth filter, cartridge filter, activated carbon filtration, demineralization and remineralization, reverse osmosis, ozonisation, ultraviolet treatment and packed. The packaged drinking water is disinfected to a level that will not lead to harmful contamination in the drinking water. It may be disinfected by means of one of chemical agents and physical methods to reduce the number of microorganism to a level that does not compromise water safety or suitability. In the process, water loses its natural taste and flavor.

In order to provide safe packaged drinking water with better flavor to people, many innovative flavors of packaged drinking water have been created. Examples of flavors include berry flavor, fruit flavor, lime flavor, spice flavor and the like. These flavors are also sometimes complemented with one or more artificial sweeteners, natural sweeteners, vitamins, minerals, fibers, spice infusions, acidulants and emulsifiers. However, these flavored packaged drinking waters still do not provide any additional health benefits to people along with the drinking water. On the other hand, herbs have been known to provide health benefits to people. The health benefits can be in the form of complete health benefits, partial health benefits or psychological health benefits. Many herbal drinks are available in the market to serve the segment of people specifically trying to look for a health drink of herbal nature. However, this has limited the usage of herbal products only to people who suffer from a health problem.

In the present scenario, there is a need for a formulation of drinking water, in particular for a formulation of packaged drinking water, which can address this problem of providing additional health benefits to people, along with providing a better taste and flavor to the water. Also, there is a need for a formulation of packaged drinking water, which can provide the benefits of herbs to a larger population and can work as a replacement for the regular drinking water.

SUMMARY OF THE INVENTION

The present invention provides a water formulation with herbal hint and a method therefore, wherein the water is generally a drinking water and the drinking water can be packaged. The drinking water with herbal hint serves the purpose of providing additional health benefits to people along with drinking water. Also, the drinking water with herbal hint provides a better taste and flavor than plain treated drinking water. The drinking water can be packaged.

In accordance with one embodiment of the present invention, the formulation of packaged drinking water with herbal hint includes water, where the water satisfies the pre-specified standards of drinking water except the odor characteristics. The formulation further includes one or more herbal ingredients. Further, the formulation includes Rosemary for stabilizing the formulation. In another embodiment, the formulation includes essential oil of Rosemary.

The one or more herbal ingredients can be selected from a group comprising essential oils in the concentration up to $5 \times 10^{-2}$ ml per L, fresh herbs in the concentration up to 20% [w/w], dried herbs in the concentration up to 10% [w/w], solar dried herbs in the concentration up to 10% [w/w], and herbal extracts in the concentration up to $5 \times 10^{-2}$ ml per L.

In accordance with an embodiment of the present invention, herbal ingredients may be selected from a group including Vetiver, *Mentha*, Rosemary, *Ocimum*, Ajowan, Geranium, Palmarosa, Celery, Salvia, Thyme, Coriander, Cardamom, Cinnamon, Clove, Ginger, Patchouli, Fennel, Lavender, Lemon, Lime, Orange, Jasmine, Chamomile, Nutmeg, Cumin and the like.

The formulation can further comprise carbon dioxide, wherein the formulation can be carbonated with carbon dioxide.

The formulation can further comprise one or more sweetening agents, wherein the one or more sweetening agents can be selected from a group comprising artificial sweetening agents in the concentration range of $1 \times 10^{-5}$ g to $2 \times 10^{-1}$ µg per L and natural sweetening agents in the concentration range up to $1.46 \times 10^{-1}$ M.

The artificial sweetening agents can be selected from the group comprising Sucralose, Aspartame, Saccharin, Acesulfame potassium, Neotame, and D-Tagatose.

The natural sweetening agents can be selected from the group comprising Sucrose, Xylitols, Polyols like sorbitol, Mannitol, Maltitol, Invert sugar, Honey and Steviosides herbal sweeteners.

The formulation can further comprise one or one or more salts, wherein the one or more salts can be selected from a group comprising table salt in the concentration range of $4.2 \times 10^{-7}$ M to $8.9 \times 10^{-4}$ M, rock salt in the concentration up to $8.9 \times 10^{-4}$ M, mineral salts of nutritional importance in the concentration up to $8.9 \times 10^{-4}$ M and vegetable salt in the concentration range of $4.2 \times 10^{-7}$ M to $8.9 \times 10^{-4}$ M.

The formulation can further comprise one or more colors, wherein the one or more colors can be selected from a group comprising artificial colors, herbal colors, and natural colors.

The formulation can further comprise one or more emulsifiers in the concentration up to $1 \times 10^{-1}$ g per L, wherein the one or more emulsifiers can be selected from the group comprising natural emulsifiers in the concentration up to $1 \times 10^{-1}$ g per L, food emulsifiers in the concentration up to $1 \times 10^{-1}$ g per L and artificial emulsifiers in the concentration up to 0.5% v/v.

The formulation can further comprise one or more pre-biotics for imparting pre-biotic activity in water, wherein the one or more pre-biotics are selected from a group comprising inulin, FOS, resistant maltodextrin, resistant dextrin, indigestible dextrin and resistant starch.

In accordance with an embodiment of the present invention, the formulation of drinking water with herbal hint includes water, where the water satisfies the pre-specified standards of drinking water except the odor characteristics. The drinking water with herbal hint can be packaged. The formulation further includes Rosemary. The formulation can include essential oil of Rosemary. The formulation further includes one or more essential oils selected from a group consisting of Vetiver, Geranium, Palmarosa and Patchouli. Further, the formulation includes one or more antioxidants for stabilizing the formulation.

The one or more antioxidants can be selected from a group comprising artificial antioxidants in the concentration up to $2 \times 10^{-1}$ g per L, natural antioxidants in the concentration up to $2 \times 10^{-1}$ ml per L and herbal antioxidants in the concentration up to $2 \times 10^{-1}$ ml per L.

The one or more antioxidants can be selected from a group comprising essential oils of Rosemary, Clove, Basil, Cinnamon, Coriander, Mint, Salvia and Fennel, characteristics of which are shown in TABLE 1.

The formulation can further comprise carbon dioxide, wherein the formulation can be carbonated with carbon dioxide.

The formulation can further comprise one or more sweetening agents, wherein the one or more sweetening agents can be selected from a group comprising artificial sweetening agents in the concentration of $1 \times 10^{-5}$ g to $2 \times 10^{-1}$ g per L and natural sweetening agents in the concentration range up to $1.46 \times 10^{-1}$ M.

The artificial sweetening agents can be selected from the group comprising Sucralose Aspartame, Saccharin, Acesulfame potassium, Neotame, D-Tagatose.

The natural sweetening agents can be selected from the group comprising Sucrose, Xylitols, Polyols like sorbitol, Mannitol, Maltitol Invert sugar, Honey and Steviosides herbal sweeteners.

The formulation can further comprise one or one or more salts, wherein the one or more salts can be selected from a group comprising table salt in the concentration range of $4.2 \times 10^{-7}$ M to $8.9 \times 10^{-4}$ M, rock salt in the concentration range up to $8.9 \times 10^{-4}$ M, mineral salts of nutritional importance in the concentration range of Zero to 8. The formulation can further comprise one or more colors, wherein the one or more colors can be selected from a group comprising artificial colors, herbal colors, and natural colors.

The formulation can further comprise one or more emulsifiers, wherein the one or more emulsifiers can be selected from the group comprising natural emulsifiers in the concentration range up to $1 \times 10^{-1}$ g per L, food emulsifiers in the concentration range up to $1 \times 10^{-1}$ g per L and artificial emulsifiers in the concentration range up to 0.5% v/v.

The formulation can further comprise one or more pre-biotics for imparting pre-biotic activity in water, wherein the one or more pre-biotics are selected from a group comprising inulin, Fructo-Oligo-Saccharides (FOS), resistant maltodextrin, resistant dextrin, indigestible dextrin and resistant starch.

In accordance with another embodiment of the present invention, a method for preparing a formulation of drinking water with herbal hint is provided. The method can be a method for preparing a formulation of packaged drinking water with herbal hint. The water is procured to satisfy the pre-specified standards of the drinking water. Thereafter, one or more herbal ingredients are added at required levels to the water. Further, Rosemary is added to the water to stabilize the formulation. Rosemary can be added to the water in the form of essential oil of Rosemary to stabilize the formulation. The water is then mixed to obtain a uniform formulation. The above water can be packed into a plurality of aseptic containers.

In one embodiment of the invention, the method can be a method for preparing a formulation of packaged drinking water with herbal hint, the method comprising the steps of: a) procuring water, wherein the water satisfies the pre-specified standards of drinking water, b) adding one or more herbal ingredients at required levels to the water, c) adding essential oil of Rosemary to the water to stabilize the formulation, d) mixing the water to obtain a uniform formulation, and e) packing the water obtained from mixing into a plurality of aseptic containers.

The method can further comprise carbonating the packaged drinking water.

The method can further comprise adding one or more sweetening agents.

The method can further comprise adding one or more salts.

The method can further comprise adding one or more colors.

The method can further comprise adding one or more emulsifiers.

The method can further comprise adding one or more pre-biotics.

DETAILED DESCRIPTION OF THE INVENTION

Before describing in detail the particular method of obtaining and formulation of drinking water with herbal hint, in particular packaged drinking water with herbal hint, in accordance with the present invention, it should be observed that the present invention resides primarily in combinations of method steps and formulation ingredients related to formulating drinking water with herbal hint. In particular, the drinking water with herbal hint can be packaged drinking water with herbal hint.

In this document, relational terms such as 'first' and 'second', and the like may be used solely to distinguish one entity or action from another entity or action without necessarily requiring or implying any actual such relationship or order between such entities or actions. The terms 'comprises', 'comprising', or any other variation thereof, are intended to cover a non-exclusive inclusion, such that a process, method, article, ingredient or apparatus that comprises a list of elements does not include only those elements but may include other elements not expressly listed or inherent to such process, method, article, or apparatus. An element proceeded by 'comprises a' does not, without more constraints, preclude the existence of additional identical elements in the process, method, article, or apparatus that comprises the element.

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

The present invention can be practiced to produce drinking water with herbal hint. In particular, the present invention can be practiced to produce packaged drinking water with herbal hint. In an embodiment of the present invention, the water required for formulation of the packaged drinking water with herbal hint is procured from one or more sources. Examples of the one or more sources include spring water, well water, river water, purified water, artesian water, fluoridated water, ground water, treated water, municipal water, mineral water, sparkling water and sterile water.

Further, there is a plurality of pre-specified standards of drinking water in existence. Examples of pre-specified standards of drinking water include guidelines set by WHO (World Health Organization), BIS (Bureau of Indian Standards) standards for packaged drinking water, EU (European Union) drinking water standards and guidelines set by US EPA (United States Environment Protection Agency). The water procured from the one or more resources is then treated through physical and chemical means to make the water comply with the pre-specified standards of the drinking water. Examples of treatments include decantation, filtration, combination of filtration, aerations, filtration with membrane filter, depth filter, cartridge filter, activated carbon filtration, demineralization and remineralization, reverse osmosis, ozonisation, ultraviolet treatment and the like.

The water is disinfected to a level that will not lead to harmful contamination in the drinking water. It may be disinfected by means of one or more of chemical agents and physical methods to reduce the number of microorganism to a level that does not compromise water safety and suitability. The packaged drinking water shall conform to the pre-specified standards namely with respect to physical, chemical and microbiological parameters.

In an embodiment of the present invention, the water that satisfies the pre-specified standards of drinking water is then mixed with Rosemary and one or more herbal ingredients. In particular, the water that satisfies the pre-specified standards of drinking water can then be mixed with essential oil of Rosemary and one or more herbal ingredients. Addition of the herbal ingredients into water can have positive health effects. The herbal ingredients can be added in the form of one or more essential oils (concentration range: up to $5\times10^{-2}$ ml per L), fresh herbs (concentration range: up to 20% [w/w]), dried herbs (concentration range: up to 10% [w/w]), solar dried herbs (concentration range: up to 10% [w/w]), and herbal extracts (concentration range: up to 6% v/v). Examples of herbal ingredients, which can be used for flavoring the water are, vetiver (*Vetiveria zizanoides*), mentha species (*Mentha piperita, Mentha arvensis, Mentha spicata* and *Mentha citrata*), rosemary (*Rosemarinus officinalis*), ocimum species (*Ocimum sanctum, Ocimum basilicum*), ajowan (*Carum copticum*), geranium species (*Pelargonium graveolens*), palmarosa (*Cymbopogon martinii*), celery seed, *salvia* species, thyme (*Thymus vulgaris*), coriander seed, cardamom (*Elettaria cardamomum*), cinnamon leaf or bark, oregano, clove (*Eugenia caryophyllata*), ginger (*Zinziber officinale*), patchouli (*Pogostemon cablin*) and the like. The specifications of the essential oils are shown in TABLE 1.

Herbs are well known and documented for their potential medicinal and various positive health inducing effects. For example, oregano oil is useful for treating digestive problems. Various herbal extracts and essential oils are used under disease specific conditions and the routine use of the same is very much restricted.

Figure 1:
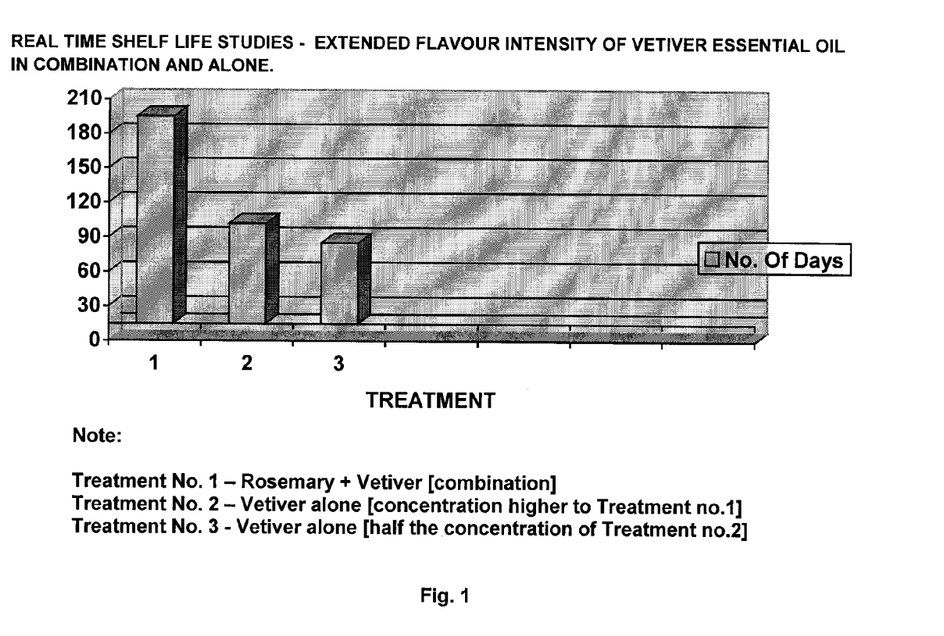
FIG. 1 depicts Synergistic effect of Rosemary in combination with Vetiver in improving sensory properties.
Figure 2:
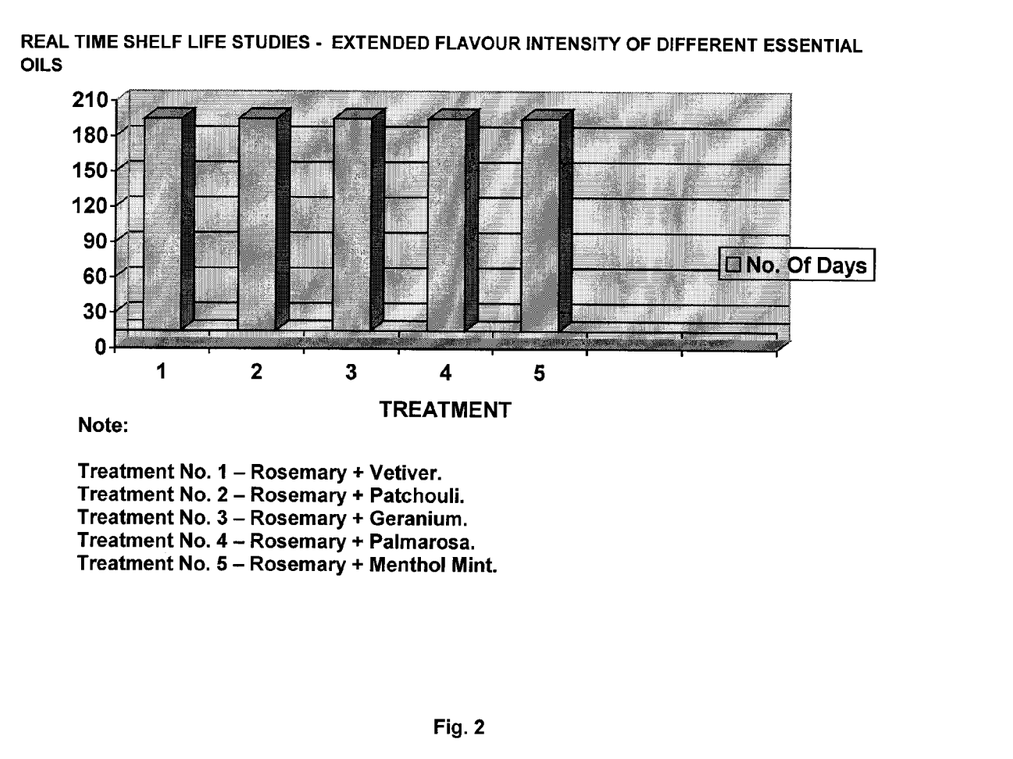
FIG. 2 depicts Synergistic effect of combination of different essential oils with Rosemary, in improving stability of the formulations.
Figure 3:
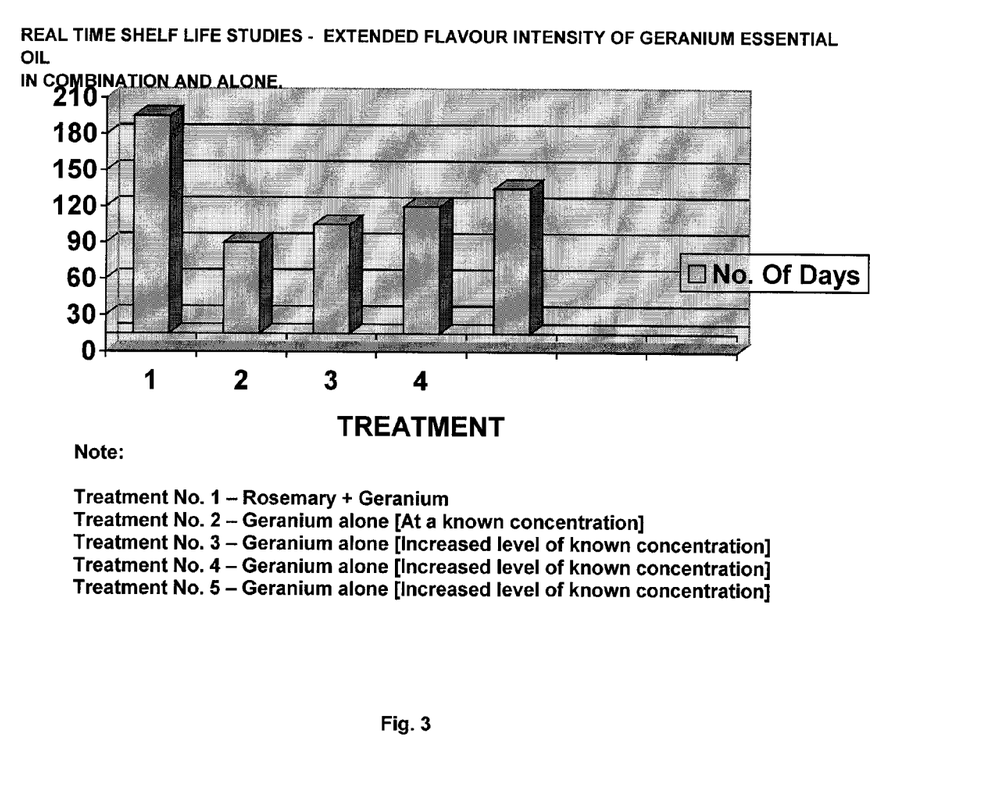
FIG. 3 depicts Synergistic effect of Rosemary in combination with Geranium, in improving sensory properties.
Figure 4:
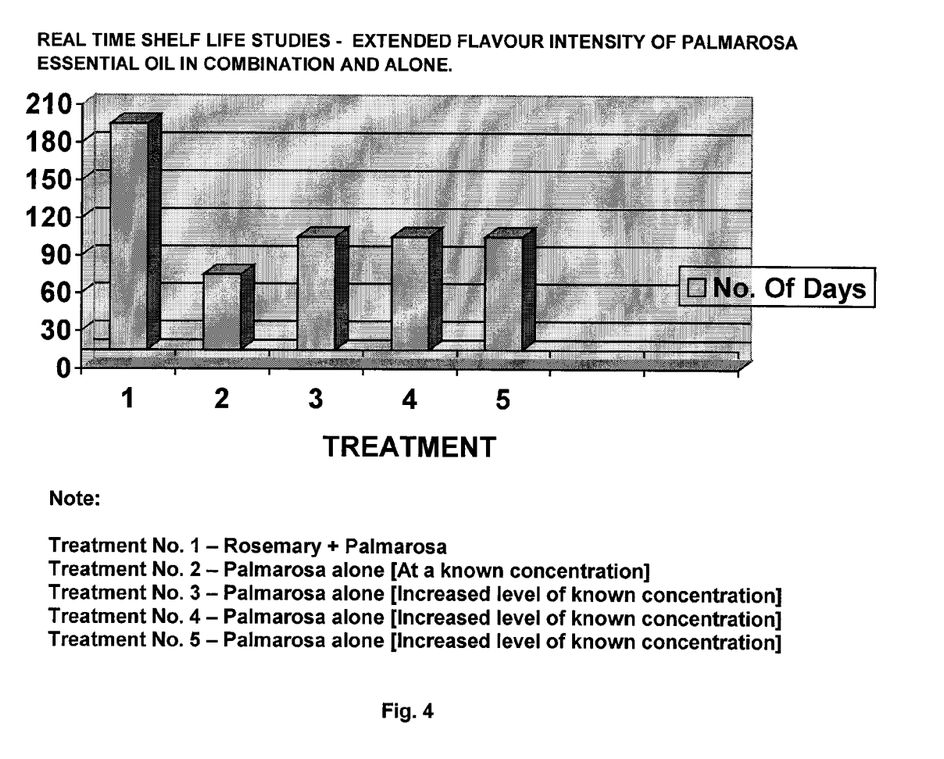
FIG. 4 depicts Synergistic effect of Rosemary in combination with Palmarosa, in improving sensory properties.
Figure 5:
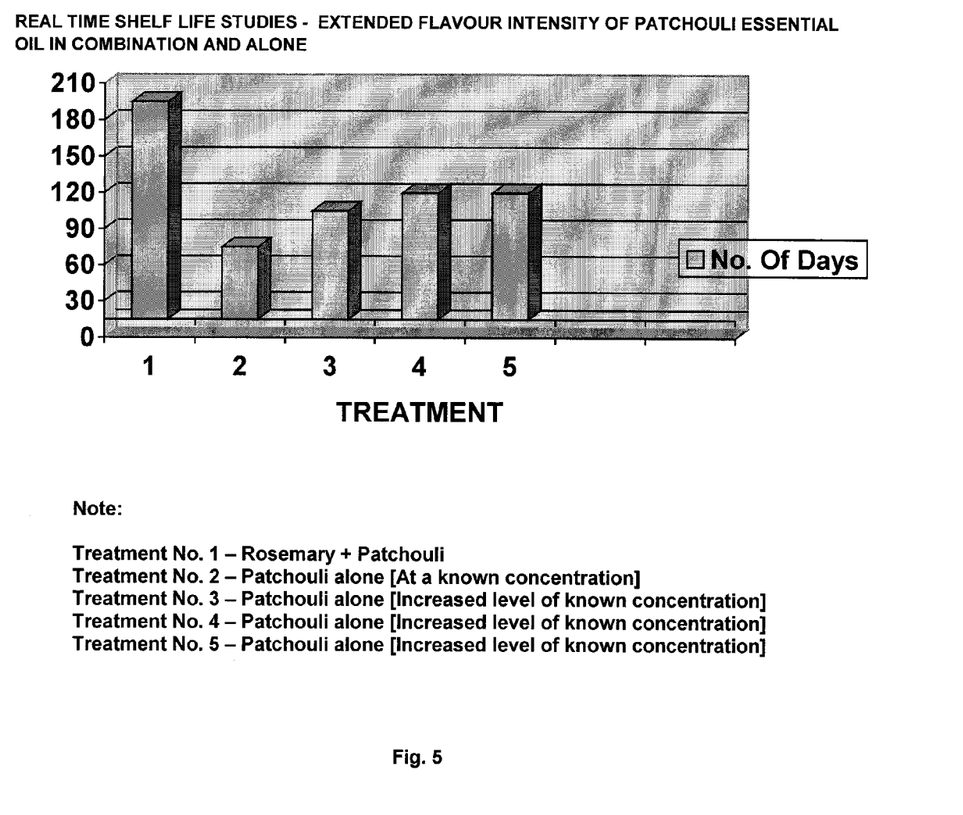
FIG. 5 depicts Synergistic effect of Rosemary in combination with Patchouli, in improving sensory properties.
Figure 6:
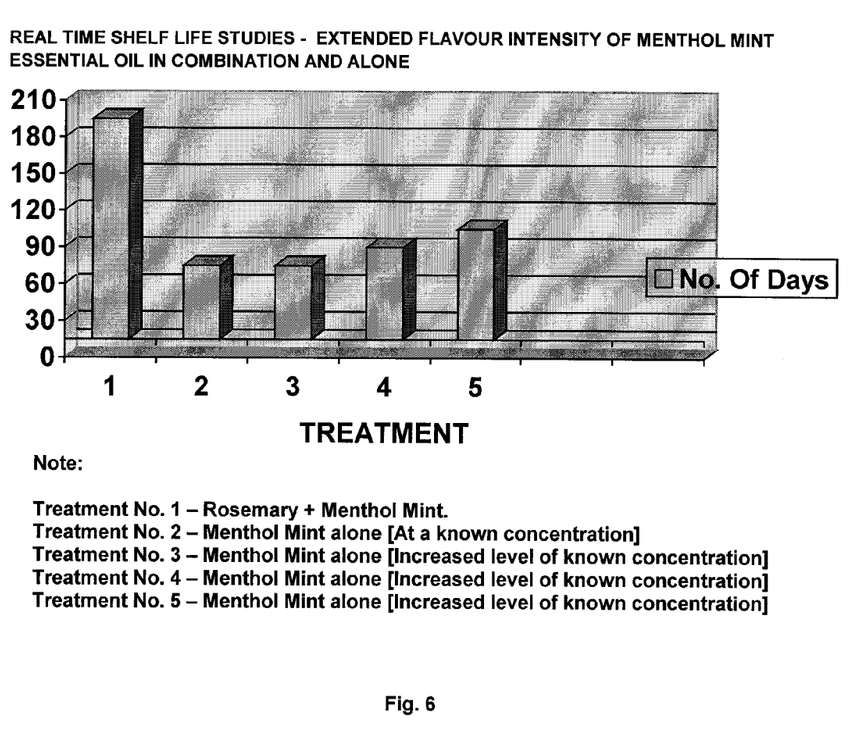
FIG. 6 depicts Synergistic effect of Rosemary in combination with Menthol Mint, in improving sensory properties

Rosemary in the form of essential oil is added into water in the concentration up to $1\times10^{-1}$ ml per L, preferably $1\times10^{-4}$ ml per L to $1\times10^{-2}$ ml per L, more preferably $1\times10^{-3}$ ml per L to $1\times10^{-2}$ ml per L. Addition of Rosemary stabilizes the formulation. Addition of essential oil of Rosemary stabilizes the formulation. With an objective of determining the shelf life of their formulation, studies were conducted to arrive at shelf life of the formulations. Pre-standardized treatments with acceptable palatability of essential oils, alone and in combination with rosemary essential oil were selected for the study. Formulation with a single essential oil at pre standardized level served as the control, while individual essential oils with acceptable palatability in combination with rosemary served as treatment. The final formulations of various flavours were stored in 1 L PET bottles, at ambient conditions with sufficient number of bottles for observation. The individual essential oils used were, Vetiver (*Vetiveria zizanoides*), Menthol Mint (*Mentha arvensis*), Geranium (*Pelargonium graveolens*), Palmarosa (*Cymbopogon martini*), Patchouli (*Pogostemon cablin*), Ocimum species (*Ocimum sanctum/Ocimum basilicum*), Lemon, Orange, Ginger, Cardamom, Peppermint, Cinnamon. The results of these studies are shown in Table 2 (Excel sheet) and in FIGS. 1 to 6 accompanying this specification.

Periodically, at 15 days interval, the samples were evaluated for their sensory profile by the panel of experts for its organoleptic quality (acceptable/not acceptable). The samples were also subjected to visual observation for its physical conditions such as, any growth, color and clarity and as a part of chemical analysis, pH determination were recorded. The pH values of the formulations ranged from 6.24-7.70, with a mean value of 6.62.

In the course of observation, it was noticed that in control samples wherein in some individual essential oils used to impart palatability, developed some cottony white strands/mass after an interval of 75 days of storage in one case, and in others after 105 days interval. The tendency of decrease in flavor profile was also noticed in control samples affecting the flavor note. While in the case of treatments, viz., in combination of essential oils with rosemary, no such abnormalities was noticed. Therefore, it is evidenced that, the combination of rosemary, in particular the combination of essential oil of rosemary with other essential oils at prescribed levels was found to have synergy, not only in improving the shelf life with good keeping quality, but also in improving the sensory properties of the formulation. Both of improved shelf life and improved sensory properties are examples of beneficial, unexpected, surprising technical effects the invention can provide.

Thus, the inventors have shown that herbal drinking water formulations according to the invention, in particular formulations comprising essential oil of Rosemary in combination with another essential oil, such as essential oil of Vetiver, Geranium, Patchouli or Menthol Mint, have significantly enhanced shelf lifes, as compared to the respective controls, as can be seen from Table 2 and FIGS. 1 to 6.

In addition, said herbal drinking water formulations also display significantly enhanced sensory properties and significantly enhanced overall acceptability, as compared to the respective controls, as can be seen from Table 2 and FIGS. 1 to 6.

In another embodiment of the present invention, essential oil of Rosemary and other essential oils are added to the water, wherein the other essential oils are selected from a group consisting of Vetiver, Geranium, Palmarosa and Patchouli. Essential oil of Rosemary can be added in the concentration up to $1 \times 10^{-1}$ ml per L, preferably $1 \times 10^{-4}$ ml per L to $1 \times 10^{-2}$ ml per L, more preferably $1 \times 10^{-3}$ ml per L to $1 \times 10^{-2}$ ml per L. The other essential oils can be added in the concentration up to $5 \times 10^{-1}$ ml per L, preferably $1 \times 10^{-4}$ ml per L to $5 \times 10^{-2}$ ml per L, more preferably $1 \times 10^{-3}$ ml per L to $5 \times 10^{-2}$ ml per L.

The herbal water formulations according to the invention can provide health benefits. The health effects of herbal water formulations according to the invention can be in the form of complete health benefits, partial health benefits, aromatic benefits or psychological health benefits. The herbal ingredients used in the present invention can provide therapeutic value to the herbal water.

The herbal water formulations according to the invention can alleviate the symptoms of uncomfortable or pathological conditions or diseases. The herbal water formulations according to the invention can be of medical use. The herbal water formulations according to the invention can be used as a medicament. The herbal water formulations according to the invention can be used in the treatment of a number of uncomfortable or pathological conditions or diseases.

The herbal water formulations according to the invention are primarily for, but not limited to, oral administration. The herbal water formulations according to the invention can also be for topical administration.

In one embodiment of the invention, a herbal drinking water formulation according to the invention that comprises essential oil of Vetiver can help in stimulating the production of red blood cells (RBCs) and can have benefits in the treatment of anemia.

In another embodiment, a herbal drinking water formulation according to the invention that comprises essential oil of Geranium can help in relieving partial menopausal symptoms like hot flashes, night sweats and mood swings and throat infections.

In another embodiment, a herbal drinking water formulation according to the invention that comprises essential oil of Palmarosa can work as a febrifuge, i.e. it can help in alleviating fever.

In another embodiment, a herbal drinking water formulation according to the invention that comprises essential oil of Patchouli can help to reduce anxiety and depression, and it can also be used for the treatment of high blood pressure.

In one embodiment of the invention, antioxidants can be added to the water to stabilize the formulation. The antioxidants are added to increase the shelf life of the herbal water so that it can be preserved for a long time. Examples of antioxidants include Rosemary, Clove, Basil, Cinnamon, Coriander, Mint, Salvia, Fennel and essential oils thereof. The antioxidants can be selected from a group comprising artificial antioxidants in the concentration up to $2 \times 10^{-1}$ g per L, natural antioxidants in the concentration range of up to $2 \times 10^{-1}$ g per L and herbal antioxidants up to $2 \times 10^{-1}$ g per L per L. Rosemary, in particular essential oil of Rosemary, is an herbal ingredient with antioxidant properties. Rosemary as an ingredient, in particular essential oil of Rosemary, provides stability to the water as far as the shelf life of the water is concerned. The shelf life of water containing essential oil of rosemary was tested to be six months.

In another embodiment of the present invention, the quantity of the herbal ingredients added to the water can be such that the water becomes palatable and biologically effective. By biologically effective it is meant that the drinking water after being mixed with the herbal ingredients has positive health effects on human beings. The positive health effects of herbal water formulations according to the invention can be in the form of complete health benefits, partial health benefits, aromatic benefits or psychological health benefits. The herbal ingredients can be added in the form of essential oils, fresh herbs, dried herbs, solar dried herbs, or herbal extracts.

The mixing of the herbal ingredients with the water can be done by one or more mixing methods. Examples of the mixing methods include using mechanical stirrers, ultrasonic technology, sonicators, industrial high shear homogenizers, blending systems and the like.

In an embodiment of the present invention, additives can be added to the herbal water. The additives can be added to make the herbal water palatable, preservable and mineralized. Examples of additives may include sweetening agents, antioxidants, salts, carbon dioxide and emulsifiers. Product specifications are shown in TABLE 1. The sweetening agents are added to improve the taste of the water. The sweetening agents may be artificial sweetening or natural sweetening agents. In an embodiment of the invention, artificial sweetening agents in the concentration up to $2 \times 10^{-1}$ g per L are added to the water. The artificial sweeteners may be Sucralose, Aspartame, Saccharin, Acesulfame potassium, Neotame, D-Tagatose and the like. In another embodiment of the invention, natural sweetening agents in the concentration up to $1.46 \times 10^{-1}$ M are added to the water. The natural sweetening agents may be Sucrose, Xylitols, Polyols like sorbitol, Mannitol, Maltitol, Invert sugar, Honey, Steviosides herbal sweeteners and the like. These sweetening agents provide same intensity of sweetness of table sugar or equivalence.

Salts can be added to the water to provide essential minerals. Types of salts may include table salt in the concentration range of $4.2 \times 10^{-7}$ M to $8.9 \times 10^{-4}$ M, rock salt in the concentration up to $8.9 \times 10^{-4}$ M, mineral salts of nutritional importance in the concentration up to $8.9 \times 10^{-4}$ M and vegetable salt in the concentration range of $4.2 \times 10^{-7}$ M to $8.9 \times 10^{-4}$ M.

Emulsifiers can be added to the water to provide uniform emulsion. Types of emulsifiers may include natural emulsifiers in the concentration up to $1 \times 10^{-1}$ g per L, food emulsifiers in the concentration range of up to $1 \times 10^{-1}$ g per L and artificial emulsifiers in the concentration up to 0.5% v/v. Examples of emulsifiers include emulsifiers made from palm oil, rapeseed oil, soybean oil, sunflower oil, partial esters of fatty acids and polyols, gum acacia, gum arabic, ester gum, alcohol, soy lecithin, xanthan gum, whey protein concentrate, sucrose ester, polyglycerol ester, polysorbates, monoglycerides, sucrose acetate iso-butyrate and the like. Colors can be added to the water to provide an aesthetic sense. Examples of colors may include artificial colors, herbal colors, natural colors and the like.

TABLE 1

NAME OF THE ESSENTIAL OIL: Vetiver oil.

| Sl No. | DESCRIPTION | |
|---|---|---|
| 1 | Common Name | Vetiver oil. |
| 2 | Botanical Name | Vetiveria zizanoides. |
| 3 | Geographic origin of the plant | Western ghats - Karnataka |
| 4 | Method of growing | Wild and cultivated |
| 5 | Method of extraction and part of the plant | Oil is obtained by steam distillation. Root. |
| | PHYSICO-CHEMICAL PROPERTIES | |
| 6 | Appearance | Viscous liquid. |
| 7 | Colour | Yellowish-Brown. |
| 8 | Aroma | Warm and specific. |
| 9 | Specific gravity | 1.008 to 1.015 at 25° C. |
| 10 | Refractive Index | 1.5203 at 25° C. |
| 11 | Optical rotation | No data |
| 12 | Acid Number | 8.60 |
| 13 | Ester Number | 18.40 |
| 14 | Storage | Store in a cool dry place |
| 15 | Expiry | 3 years from the date of manufacture. |

NAME OF THE ESSENTIAL OIL: Geranium oil.

| Sl No. | DESCRIPTION | |
|---|---|---|
| 1 | Common Name | Geranium oil. |
| 2 | Botanical Name | Pelargonium sps. |
| 3 | Geographic origin of the plant | Not known. |
| 4 | Method of growing | Cultivated. |
| 5 | Method of extraction and part of the plant | Oil is obtained by steam distillation. Aerial parts. |
| | PHYSICO-CHEMICAL PROPERTIES | |
| 6 | Appearance | Liquid. |
| 7 | Colour | Light Yellowish. |
| 8 | Aroma | Specific. |
| 9 | Refractive Index | 1.4648 at 25° C. |
| 10 | Optical rotation | −8.5° to 17.50° |
| 11 | Acid Number | Not known |
| 12 | Ester Number | Not known |
| 13 | Expiry | 3 years from the date of manufacture. |

NAME OF THE ESSENTIAL OIL: Palmarosa oil.

| Sl No. | DESCRIPTION | |
|---|---|---|
| 1 | Common Name | Palmarosa oil. |
| 2 | Botanical Name | Cymbopogon martini var.motai |
| 3 | Geographic origin of the plant | Maharashtra - India. |
| 4 | Method of growing | Cultivated. |
| 5 | Method of extraction and part of the plant | From freshly cut whole flowering plant. |
| | PHYSICO-CHEMICAL PROPERTIES | |
| 6 | Appearance | Slightly viscous liquid. |
| 7 | Colour | Light Yellowish. |
| 8 | Aroma | Specific. |
| 9 | Specific gravity | 0.88 to 0.91 at 25° C. |
| 10 | Refractive Index | 1.47 to 1.48 at 25° C. |
| 11 | Optical rotation | −0.5° to +0.75° at 25° C. |
| 12 | Acid Number | 0.85 to 10.85 |
| 13 | Ester Number after acetylation | 240-305 |
| 14 | Expiry | 3 years from the date of manufacture. |

NAME OF THE ESSENTIAL OIL: Patchouli oil.

| Sl No. | DESCRIPTION | |
|---|---|---|
| 1 | Common Name | Patchouli oil. |
| 2 | Botanical Name | Pogostemon cablin Benth. |
| 3 | Geographic origin of the plant | Karnataka |
| 4 | Method of growing | Cultivated. |
| 5 | Method of extraction and part of the plant | From freshly cut whole flowering plant. |
| | PHYSICO-CHEMICAL PROPERTIES | |
| 6 | Appearance | Liquid. |
| 7 | Colour | Light Yellowish. |
| 8 | Aroma | Specific. |
| 9 | Specific gravity | 0.97 to 0.99 at 20° C. |
| 10 | Refractive Index | 1.48 to 1.51 at 25° C. |
| 11 | Optical rotation | — |
| 12 | Acid Number | — |
| 13 | Ester Number | — |
| 14 | Expiry | 3-5 years from the date of manufacture. |

NAME OF THE ESSENTIAL OIL: Menthol Mint oil.

| Sl. No. | DESCRIPTION | |
|---|---|---|
| 1 | Common Name | Menthol mint oil. |
| 2 | Botanical Name | Mentha arvensis L. |
| 3 | Geographic origin of the plant | Karnataka. |
| 4 | Method of growing | Cultivated. |
| 5 | Method of extraction and part of the plant | Oil is obtained by steam distillation. Aerial parts. |
| | PHYSICO-CHEMICAL PROPERTIES | |
| 6 | Appearance | Colour less liquid. |
| 7 | Colour | Transparent. |
| 8 | Aroma | Specific. |
| 9 | Specific gravity | 0.89 to 0.90 at 25° C. |
| 10 | Refractive Index | 1.45 to 1.47 at 25° C. |
| 11 | Optical rotation | −15.5° to −45.0 at 25° C. |
| 12 | Acid Number | 0.3 to 5. |
| 13 | Ester Number | 210 to 255. |
| 14 | Expiry | 3 years from the manufacture date. |

NAME OF THE ESSENTIAL OIL: Basil/Tulasi oil.

| Sl. No. | DESCRIPTION | |
|---|---|---|
| 1 | Common Name | Tulasi/Holy basil. |
| 2 | Botanical Name | Ocimum sanctum |
| 3 | Geographic origin of the plant | Karnataka |
| 4 | Method of growing | Wild and cultivated. |
| 5 | Method of extraction and part of the plant | Oil is obtained by steam distillation. Aerial parts. |
| | PHYSICO-CHEMICAL PROPERTIES | |
| 6 | Appearance | Liquid. |
| 7 | Colour | Light Yellowish. |
| 8 | Aroma | Specific. |
| 9 | Specific gravity | 0.87 to 0.90 at 25° C. |
| 10 | Refractive Index | 1.46 to 1.48 at 25° C. |
| 11 | Optical rotation | −8.5° to 17.50° |
| 12 | Acid Number | Not more than 4.0 |
| 13 | Ester Number | 4.0 to 15.0 |
| 14 | Storage | Keep in well-sealed containers at 5 to 15° C. without direct exposure to sunshine or heat sources. |
| 15 | Expiry | 3 years from the manufacture date. |

PRODUCT SPECIFICATION
NAME OF THE PRODUCT: SPRAY DRIED GUM ARABIC/GUM ACACIA

| Sl No. | DESCRIPTION | |
|---|---|---|
| 1 | Physical characteristics/appearance | Light brown, free flowing powder, odourless and bland in taste. |
| 2 | Loss on drying | Not more than 10%. |
| 3 | Specific optical rotation | +10° to +60° |

TABLE 1-continued

| | | |
|---|---|---|
| 4 | Colour Value (25% soln.) | 45 to 55 |
| 5 | Viscosity (25% soln.) | 100 to 150 cps. |
| 6 | Specific gravity (25% soln.) | 1.05 to 1.15. |
| 7 | Turbidity (2% soln.) | nmt. 40 NTU |
| 8 | pH (25% soln.) | 4 to 4.50 |
| 9 | Water Insoluble matter | 0.5% max. |
| 10 | Total ash | 4% max. |
| 11 | Acid insoluble ash | 0.5% max. |
| 12 | Heavy metals | 20 ppm max. |
| 13 | Storage | Cool and dry place below 25° C. |
| 14 | Shelf life | 4 yrs in original packing. |
| MICROBIOLOGICAL PARAMETERS | | |
| 15 | Total Plate Count | <500 CFU/g. |
| 16 | Yeast & Moulds | <50 CFU/g. |
| 17 | *Salmonella* | Absent |
| 18 | *E. coli* | Absent |

NAME OF THE PRODUCT: VEGETABLE SALT.

| Sl No. | DESCRIPTION | Saloni | Saloni-k (Low sodium salt of Botanic origin) |
|---|---|---|---|
| 1 | Physical characteristics/appearance | White, free flowing | White, free flowing, free from additives. |
| 2 | Loss on drying | Not available | Not available |
| Elemental concentration | | | |
| | Element | | |
| 3 | NaCl (%) | 89-92 | 65-70 |
| 4 | KCl (%) | 5-8 | 25-30 |
| 5 | Ca (%) | 0.2-0.4 | 0.2-0.3 |
| 6 | Mg (%) | 0.02-0.08 | 0.02-0.03 |
| 7 | SO4 | 2.2-2.8 | 1.1-2.04 |
| 8 | Iodine (ppm) | 7-10 | 5-7 |
| 9 | Iron (ppm) | 3-10 | 3-12 |
| 10 | Copper (ppm) | 1-5 | 0.5-4.0 |
| 11 | Zinc (ppm) | 1.0-5.0 | 1.0-5.0 |
| 12 | Nickel | *BDL | BDL |
| 13 | Cobalt | BDL | BDL |
| 14 | Arsenic | BDL | BDL |
| 15 | Cadmium | BDL | BDL |
| 16 | Mercury | BDL | BDL |
| 17 | Lead | BDL | BDL |
| 18 | Antimony | BDL | BDL |

*BDL—Below detection Limit.

NAME OF THE PRODUCT: POLYSORBATE-80,
INCI NAME: POLYSORBATE-80, CHEMICAL NAME: POLYSORBATE-80 K

| Sl No. | DESCRIPTION | |
|---|---|---|
| 1 | Ingredients | Sorbitan, Mono-9-Octadece, 9005-65-6 and vitamin E alcohol, 1019-41-0 |
| Physical and Chemical properties | | |
| 2 | Melting point | No data |
| 3 | Boiling point | >300 F 1atmospheres. |
| 4 | Evaporation rate | >1 |
| 5 | Specific gravity | 1.09 at 25 degree Celsius |
| 6 | Solubility in water | Soluble. |
| 7 | Appearance & Odour | Clear yellow liquid, Mild bland odour. |

PRODUCT NAME: WHEY PROTEIN CONCENTRATE-70%
Physical Specifications:

| Sl No. | Specifications | Assay |
|---|---|---|
| 1 | 6.1-6.7 | pH (10% Solution) |
| 2 | Disc "A" | Scorched particles |
| 3 | 0.1 ml Max. | Solubility Index |
| 4 | 0.50 g/cc | Bulk Density |
| 5 | White to cream, free flowing | Colour |
| 6 | Bland | Flavour and odour |
| 7 | 30 ppm Max. | Heavy metals |

Chemical Specifications:

| Assay | Specifications | Method of analysis |
|---|---|---|
| Protein (N × 6.38) | 70-72% | AOAC 16 th Ed., Chap-50, Pg no.-15 |
| Lactose | 14-16% | AOAC 16 th Ed., Chap-50, Pg no.-15 |
| Fat | 6-8% | AOAC 16 th Ed., Chap-50, Pg no.-15 |
| Ash | 4% Max. | AOAC 16 th Ed., Chap-50, Pg no.-15 |
| Moisture | 3.0-4.0% | AOAC 16 th Ed., Chap-50, Pg no.-15 |

Microbiological Specifications:

| Assay | Specifications | Method of analysis |
|---|---|---|
| Total plate count (cfu/g) | <30,000/g | USP - 24: 2021 |
| Yeast & Mould | <100/g | USP - 24: 2021 |
| *E. Coli*/10 g | Absent | USP - 24: 2021 |
| *Salmonella*/10 g | Absent | USP - 24: 2021 |
| *Staphylococcus aureus*/10 g | Absent | USP - 24: 2021 |
| *Pseudomonas aeruginosa*/10 g | Absent | USP - 24: 2021 |

PRODUCT NAME: SUCRALOSE. (ARTIFICIAL SWEETENER)
Physical Specifications:

| Assay | Specifications |
|---|---|
| Appearance | White to off-white, odourless, crystalline powder |
| Colour | White |
| Dispersibility | Good |
| Wettability | <1 second |
| pH (10% w/v solution) | 5-8 |
| Specific Optical rotation (10% Solution) | +84.0°~+87.5° |
| Particle size | 100% passing through 30 mesh |

Chemical Specifications:

| Assay | Specifications |
|---|---|
| Methanol | 0.1% Max. |
| Arsenic (As) | 0.0003% Max. |
| Heavy metals (Pb) | 0.001% Max. |
| Hydrolysis products | 1.5% Max. |
| Moisture | <2.0% |

Microbiological Specifications;

| Assay | Specifications | Method of analysis |
|---|---|---|
| Total plate count (cfu/g) | <200 CFU/g | USP - 24: 2021 |
| Mould/Yeast (cfu/g) | <50 CFU/g | USP - 24: 2021 |
| Coliform bacteria | Absent | USP - 24: 2021 |
| *E. coli*/10 g | Absent | USP - 24: 2021 |
| *Staphylococcus aureus*/g | Negative | USP - 24: 2021 |
| *Salmonella*/100 g | Negative | USP - 24: 2021 |
| *Pseudomonas aeruginosa*/10 g | Absent | USP - 24: 2021 |

PRODUCT NAME: SUCROSE
Organoleptic Parameters:

| Assay | Specifications |
|---|---|
| Odour | Odourless |
| Tate | Sweet/No objectionable |

Physical Specifications:

| Assay | Specifications |
|---|---|

TABLE 1-continued

| | |
|---|---|
| Appearance | Clear white |
| Black particles | 1.5 Max. |
| Extraneous matter | Absent |

Chemical Specifications:

| Assay | Specifications |
|---|---|
| Assay purity (Total solids) (min. %) | 99.50 |
| SO2 (Min. %) | 0.05 |
| Starch (Min.) | 15 ppm |
| Partcle size | <60 Microns |
| Acid Insoluble Ash | 0.04 |
| Lead (Max.) | 2 ppm |
| Copper (Max.) | 30 ppm |

Microbiological Specifications

| Assay | Specifications | Method of analysis |
|---|---|---|
| Total plate count (cfu/g) | <1000 | USP - 24: 2021 |
| Yeast & mould (cfu/g) | <10 | USP - 24: 2021 |
| *E. coli* (/10 g) | Absent | USP - 24: 2021 |
| *Salmonella* (/10 g) | Absent | USP - 24: 2021 |
| *Staphylococcus aureus* (/10 g) | Absent | USP - 24: 2021 |
| *Pseudomonas aeruginosa* (/10 g) | Absent | USP - 24: 2021 |

PRODUCT NAME: SOY LECITHIN (NON-GMO).
Physico-Chemical properties:

| Assay | Specifications |
|---|---|
| Characteristics | A standardized liquid vegetable lecithin consisting of the mixture of polar and nonpolar lipids. |
| Composition | Mixture of non-polar (triglycerides) and polar (phospho - and glyco-) lipids and a small amount of carbohydrates. |
| Consistency | Liquid. |
| Solubility in water | Dispersible. |
| Solubility | Soluble. |
| in fats/oils | Partly soluble. |
| Solubility in ethanol | |
| Peroxide value | Max. 5 meq/1000 g |
| Acid value | Max. 30 meq/KOH/g |
| Hexane insolubles | Max. 0.3% |
| Iodine colour value (10% in Toluene) | Max. 60 |
| Viscosity (25° C.) | Max. 12,500 cps |
| Regulatory status | This product is Generally recognized as safe (GRAS) |

PRODUCT NAME: ASPARTAME (ARTIFICIAL SWEETENER)
Physicochemical properties:

| Assay | Specifications |
|---|---|
| Description | Aspartame is a nutritive sweetener. |
| Appearance | A white crystalline powder approximately 200 times sweeter than sugar. |
| Solubility in water | Sparingly soluble. |
| Solubility in alcohol | Slightly soluble. |
| Colour | White |
| Odour | Odourless |
| Taste | Sweet |
| Assay Dried Basis | 98-102% |
| Loss on Drying | Not more than 4.5% |
| Heavy Metal (as lead) | Not more than 10 mg/kg. |
| Arsenic | Not more than 3 mg/kg. |
| Specific Rotation | +14.5°-+16.5° |
| pH | 4.5-6.0 |
| Particle size | Not more than 1.0% |

MICROBIOLOGICAL PARAMETERS

| | |
|---|---|
| Total Plate count | Not more than 250 CFU/g |
| Total Fungal Count | Not more than 100 CFU/g |
| Total Coliform Count | Not more than 10 CFU/g |
| *E. coli* | Absent |
| *Salmonella* | Absent |

In an embodiment of the present invention, pre-biotics can be added to water to impart pre-biotic activity in water. Pre-biotics are defined as non-digestible food ingredients that may beneficially affect the host by selectively stimulating the growth and/or the activity of a limited number of bacteria in the colon. Examples of pre-biotics include inulin, FOS, resistant maltodextrin, resistant dextrin, indigestible dextrin and resistant starch.

In an embodiment of the present invention, after mixing the herbal ingredients and the additives with the water, the water can be packed in aseptic containers. Examples of aseptic containers include aseptic bottles, aseptic cans, aseptic jars, aseptic packets, aseptic jugs, aseptic bowls, aseptic cauldrons, aseptic flasks, aseptic drums, aseptic tubs and aseptic glasses.

The present invention may be better understood by referring to the examples set forth below.

The method pertaining to the production of drinking water, in particular to the production of packaged drinking water, includes following strict standards and safety protocols. Physico-chemical treatments like filtration, combination of filtration, aerations, filtration with membrane filter, depth filter, cartridge filter, activated carbon filtration, demineralization and remineralization, reverse osmosis, ozonisation and ultraviolet irradiation are followed to ensure the safety standards of drinking water.

One liter of the water is taken in a stainless steel mixing tank of certain capacity. The water is then mixed with rosemary oil. In an embodiment of the invention, the rosemary oil may be present in the concentration range $1 \times 10^{-3}$ ml/liter to $1 \times 10^{-2}$ ml/liter of water. In an embodiment of the invention, the water may be further mixed with other essential oils/oleoresins up to $5 \times 10^{-1}$ ml/liter. The other essential oils may be Vetiver (*Vetiveria zizanoides*), Mentha species (*Mentha piperita/Mentha arvensis/Mentha spicata* and *Mentha citrata*), Rosemary (*Rosemarinus officinalis*), Ocimum species (*Ocimum sanctum/Ocimum basilicum*), Coleus (*Coleus forskolii*), Ajowan (*Carum copticum*), Geranium species (*Pelargonium graveolens*), Palmarosa (*Cymbopogon martini*), Celery seed, Salvia species, Thyme (*Thymus vulgaris*), Coriander seed, Cardamom (*Elettaria cardamomum*), Cinnamon leaf/bark, Clove (*Eugenia caryophyllata*), Ginger (*Zinziber officinale*), Patchouli (*Pogostemon cablin*), Fennel, Lavender, Lemon, Lime, Orange, Jasmine, Chamomile, Nutmeg, Cumin, and the like.

The water is mixed thoroughly to get the uniform emulsion using various emulsifying agents like Gum Acacia ($1 \times 10^{-5}$ g to $5 \times 10^{-2}$ g/L), Gum Arabic ($1 \times 10^{-5}$ g to $5 \times 10^{-2}$ g/L), Soy Lecithin ($1 \times 10^{-5}$ g to $5 \times 10^{-2}$ g/L), Xanthan gum ($1 \times 10^{-5}$ g to $1 \times 10^{-1}$ g/L), Polysorbates (up to 0.5% v/v) and using emulsifying devices like mechanical stirrers, ultrasonic sonicators, industrial high shear Homogenizer, and ordinary blending systems. In all these devices aseptic conditions are maintained. For each of the mentioned emulsifying device, the water is blended for a minimum of 30 minutes to 2 hours. The proper blending of emulsion is judged, by periodically (with a frequency of 15 minutes) drawing the water sample and evaluating it organoleptically. Once the emulsion is prepared, a suitable device is used to transfer the mixed product to the aseptically maintained bottle filling line.

In an embodiment of the present invention, a flavour profile of end produce can be achieved by using a minimum of three mixing equipments. The individual equipments may be used to prepare single flavour or specific mixed flavour combinations. In another embodiment of the present invention, the tank is thoroughly washed with small quantity of ethyl alcohol, followed by water and subjecting the tank to dry heat treatment. Separate pipelines are used that join the mixing tanks with different bottling plants to avoid any cross mixing/contamination of flavours.

In an embodiment of the present invention, the water can be mixed with Sucrose to induce palatable sweetness.

In another embodiment of the present invention, the water may be further mixed with table salt or mineral salts of nutritional importance. After mixing of the water with table salt the water can be mixed with Gum acacia to obtain a uniform emulsion.

In another embodiment of the invention, a suitable color may be added to the water to provide aesthetic sense of the herbal ingredient.

In another embodiment of the invention, the water may be carbonated with carbon dioxide.

In another embodiment of the present invention, the herbal hint water can be fortified with pre-biotic agents like Inulin, FOS, Resistant Maltodextrin, Resistant Dextrin, Indigestible Dextrin to introduce pre-biotic component so as to provide minimal quantity of soluble fiber to improve the intestinal microflora.

The water can then packed into a plurality of aseptic containers.

With reference to the above mentioned method, the following concentrations of different ingredients were used to manufacture the drinking formulation of the present invention, in particular to manufacture the packaged drinking formulation of the present invention.

EXAMPLE 1

Water: One liter obtained from spring water meeting the pre-specified standard.
Herbal Ingredient Rosemary—concentration range $1\times10^{-3}$ ml per liter to $1\times10^{-2}$ ml per liter.
Other Herbal Ingredient: Essential oil of Palmarosa Zero to $2.5\times10^{-2}$ ml per liter.
Emulsifier: Gum Acacia/Gum Arabic: $1\times10^{-5}$ g to $5\times10^{-2}$ g per liter OR
Polysorbate: up to 0.5% v/v.

EXAMPLE 2

Water: One liter obtained from spring water meeting the pre-specified standard
Herbal Ingredient Rosemary—concentration range $1\times10^{-3}$ ml per liter to $1\times10^{-2}$ ml per liter.
Other Herbal Ingredient: Essential oil of Palmarosa—$2.5\times10^{-2}$ ml per liter.
Emulsifier: Gum Acacia/Gum Arabic: $1\times10^{-5}$ g to $5\times10^{-2}$ g per liter OR
Polysorbate: Zero to 0.5% v/v.
Sweetener: Sucrose—$2.92\times10^{-5}$ M to $1.46\times10^{-1}$ M.

EXAMPLE 3

Water: One liter obtained from spring water meeting the pre-specified standard
Herbal Ingredient Rosemary—concentration range $1\times10^{-3}$ ml per liter to $1\times10^{-1}$ ml per liter.
Other Herbal Ingredient: Essential oil of Vetiver (*Vetiveria zizanoides*), characteristics as shown in Table 2: concentrations range $1\times10^{-3}$ to $5\times10^{-2}$ ml per liter.
Emulsifier: Soy Lecithin: $1\times10^{-5}$ g to $5\times10^{-2}$ g per liter.
Table salt: Sodium Chloride/Vegetable salt: $4.2\times10^{-7}$ M to $8.9\times10^{-4}$ M.

EXAMPLE 4

Water: One liter obtained from spring water meeting the pre-specified standard.
Herbal Ingredient Rosemary—concentration range $1\times10^{-3}$ ml per liter to $1\times10^{-1}$ ml per liter.
Other Herbal Ingredient: *Ocimum* species (*Ocimum sanctum/Ocimum basilicum*), characteristics as shown in Table 2: concentration: $5\times10^{-1}$ ml per liter.
Emulsifier: Polysorbate up to 0.5% v/v.
Sweetener: Aspartame: $1\times10^{-5}$ g to $1.8\times10^{-1}$ g to induce palatable sweetness.

EXAMPLE 5

Water: One liter obtained from spring water meeting the pre-specified standard.
Rosemary oil: concentrations range $1\times10^{-4}$ ml per liter to $1\times10^{-2}$ ml per liter.
Other Herbal Ingredient: *Ocimum* species (*Ocimum sanctum/Ocimum basilicum*): concentrations range up to $5\times10^{-1}$ ml per liter.
Emulsifier: Gum Arabic: $1\times10^{-5}$ g to $5\times10^{-2}$ g per liter.
Pre-biotics: 1 to 5 g of Inulin or FOS or Resistant starch per liter.

EXAMPLE 6

Water: One liter obtained from spring water meeting the pre-specified standard.
Rosemary oil: concentrations range $1\times10^{-4}$ ml per liter to $1\times10^{-2}$ ml per liter.
Other Herbal Ingredient: Natural essential oil of Lemon/Orange concentrations range $5\times10^{-1}$ ml per liter.
Table salt: Sodium Chloride: $4.2\times10^{-7}$ M to $8.9\times10^{-4}$ M.
Acidulants: Citric Acid $2.3\times10^{-3}$ M to $7.3\times10^{-3}$ M and Malic Acid $3\times10^{-4}$ M to $9\times10^{-4}$ M.
Emulsifier: Gum Arabic: $1\times10^{-5}$ g to $5\times10^{-2}$ g per liter.

In addition to the above mentioned examples, in various embodiments of the present invention, the following ingredients may also be used to prepare the drinking water, in particular to prepare the packaged drinking water:
Artificial Sweeteners:
Sucralose: $1\times10^{-5}$ g to $6.3\times10^{-2}$ g per liter to induce palatable sweetness.
Aspartame: $1\times10^{-5}$ g to $1.8\times10^{-1}$ g to induce palatable sweetness.
Emulsifying Agent: (Natural emulsifiers and food emulsifiers)
Whey Protein Concentrate: 0.01 mg to 100 mg per liter
Emulsifying Agent: (Artificial emulsifiers)
Polysorbates: up to 0.5% v/v.
Acidulants: Citric Acid 2.3 M$\times10^{-3}$ to $7.3\times10^{-3}$ M and Malic Acid $3\times10^{-4}$ M to $9\times10^{-4}$ M.

In various embodiments of the present invention, one or more antioxidants may be added to preserve the packaged drinking water formulation for a longer time. Examples of the antioxidants may include artificial antioxidants, natural antioxidants and herbal antioxidants.

The herbal ingredients used in the present invention can provide therapeutic value to the drinking water. For example, the Tulsi plant has many medicinal properties. The leaves of Tulsi are a nerve tonic and also sharpen memory. They promote the removal of the catarrhal matter and phlegm from the bronchial tube. The leaves strengthen the stomach and induce copious perspiration, for relief. Further, the leaves of Tulsi are specific for many fevers. Thus, the invention also comprises a herbal drink essentially as described above, wherein the herbal ingredient can comprise the leaves of the Tulsi plant. In particular, the herbal ingredient of such herbal water can comprise essential oil of the Tulsi plant.

In view of the above, it can be concluded that drinking water with herbal hint, in particular that packaged drinking water with herbal hint, can serve the purpose of providing health benefits to people along with drinking water. Also, the drinking water with herbal hint according to the invention, in particular the packaged drinking water according to the invention, provides a better taste and flavor than plain treated drinking water. Since the herbal ingredients are mixed with water, it can be available to a larger population, and prove beneficial to people. In fact, it can also work as a replacement for regular drinking water. Also, the drinking water with herbal hint according to the invention can be used for various other purposes as regular drinking water, for example making mocktails, cocktails, sherbet and the like.

In the foregoing specification, specific embodiments of the present invention have been described. However, one of ordinary skill in the art appreciates that various modifications and changes can be made without departing from the scope of the present invention as set forth in the claims below. Accordingly, the specifications are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The examples under the present invention, detailed in the illustrative examples contained here, are described using herbal ingredients available as essential oils. However, use of these examples should not be interpreted to limiting the invention to that particular form of herbal ingredients and to that particular concentration of essential oils.

We claim:

1. A method for preparing an alcohol free herbal water formulation having a shelf life of six months at 25° C. and retaining its sensory properties for use as human drinking water, consisting of:
   a. adding a first essential oil of rosemary in concentration ranging from $1\times10^{-4}$ ml/L to $1\times10^{-1}$ ml/L to water satisfying pre-specified standards of drinking as prescribed under United States Environmental Protection Agency;
   b. adding another essential oil in concentration ranging up to $5\times10^{-1}$ ml/L to the water of step (a), wherein the essential oil is selected from the group consisting of:
      vetiver oil,
      geranium oil,
      palmarosa oil,
      patchouli oil, and
      menthol mint oil;
   c. adding a concentration of: up to $1\times10^{-1}$ g/L or up to 0.5% v/v of an emulsifer; and
   d. optionally adding one salt selected from the group of:
      from $4.2\times10^{-7}$ M to $8.9\times10^{-4}$ M of table salts,
      up to $5.25\times10^{-2}$ g/L of rock salt,
      up to $8.9\times10^{-4}$ M of mineral salts, and
      from $4.2\times10^{-7}$ M to $8.9\times10^{-4}$ M vegetable salt.

* * * * *